United States Patent

Knoll

[11] Patent Number: 5,846,392
[45] Date of Patent: Dec. 8, 1998

[54] MINIATURIZED CIRCULATORY MEASURING CHAMBER WITH INTEGRATED CHEMO- AND/OR BIOSENSOR ELEMENTS

[76] Inventor: Meinhard Knoll, Geschwister-Scholl-Strasse 9, DE-048565 Steinfurt, Germany

[21] Appl. No.: 702,563
[22] PCT Filed: Mar. 10, 1995
[86] PCT No.: PCT/DE95/00339
  § 371 Date: Oct. 8, 1996
  § 102(e) Date: Oct. 8, 1996
[87] PCT Pub. No.: WO95/25275
  PCT Pub. Date: Sep. 21, 1995

[30] Foreign Application Priority Data

Mar. 12, 1994 [DE] Germany .......................... 44 08 352.1

[51] Int. Cl.⁶ .................................................. G01N 27/26
[52] U.S. Cl. ...................... 204/403; 204/409; 422/82.02; 422/82.03
[58] Field of Search .................................... 204/403, 409; 422/82.02, 82.03

[56] References Cited

U.S. PATENT DOCUMENTS

| | | | |
|---|---|---|---|
| 4,874,500 | 10/1989 | Madou et al. | 204/412 |
| 4,889,611 | 12/1989 | Blough, Jr. | 204/411 |
| 5,194,133 | 3/1993 | Clark et al. | 204/299 R |
| 5,238,548 | 8/1993 | Van Der Wal et al. | 204/418 |
| 5,393,401 | 2/1995 | Knoll | 204/418 |

FOREIGN PATENT DOCUMENTS

| | | |
|---|---|---|
| 0299778 | 1/1989 | European Pat. Off. . |
| 0455508 | 11/1991 | European Pat. Off. . |
| 4115414 | 11/1992 | Germany . |
| 2236903 | 4/1991 | United Kingdom . |
| 8808973 | 11/1988 | WIPO . |
| 9221020 | 11/1992 | WIPO . |

OTHER PUBLICATIONS

Shuiji Shoji et al., "Micro Flow Cell for Blood Gas Analysis Realizing Very Small Sample Volume", *Sensors and Actuators B*, vol. B08, No. 2, pp. 205–208, XP 000286957, May 1, 1992.

Van Der Schoot et al., "An ISFET–Based microlitre titrator: Integration of a chemical sensor–actuator system", Third International Conference on Solid–State Sensors and Actuators (Transducers '85), Philadelphia, PA USA, 11–14 Jun. 1985, vol. 8, No. 1, ISSN 0250–6874, Sensors and Actuators, Sep., 1985, Switzerland, pp. 11–22.

Van Der Shoot et al., "Modular setup for a miniaturized chemical analysis system", Eurosensors VI, San Sebastian, Spain, 5–7, Oct. 1992, vol. B15, No. 1–3, ISSN 0925–4005, Sensors and Actuators B (Chemical), Aug. 1993, Switzerland, pp. 211–213.

Schwedt, *Taschentlas de Analytik* (1992), pp. IV and V, no month available.

Schmidt et al., "Calibration of a Wearable Glucose Sensor," *The International Journal of Artificial Organs*, 15, pp. 55–61 (1992), no month available.

Scheller et al., *Biosensoren* (1989), pp. V–VII, no month available.

Schwedt, *Taschentlas de Analytik* (1992), pp. IV, V, and 190–195.

Scheller et al., *Biosensoren* (1989), pp. V and 48–67.

*Primary Examiner*—Bruce F. Bell
*Attorney, Agent, or Firm*—Greenblum & Bernstein, P.L.C.

[57] ABSTRACT

A miniaturized circulatory measuring chamber with integrated chemo- and/or biosensor elements including a substrate formed from a plate-shaped carrier. Within the plate-shaped carrier is inserted at least one containment tapering from a frontal surface of the plate-shaped carrier toward a second surface. At least one plate is connected to the second surface. At least one duct-shaped cavity is in contact with a small opening of the containment.

24 Claims, 5 Drawing Sheets

MINIATURIZED CIRCULATORY MEASURING CHAMBER WITH INTEGRATED CHEMO- AND/OR BIOSENSOR ELEMENTS

This application is a 371 of PCT/DE95/00339 filed on Mar. 10, 1995.

BACKGROUND OF THE INVENTION

1. Field of the Invention

The invention relates to a miniaturized circulatory measuring chamber with integrated chemo- and biosensor elements, to a method for its production and to its utilization.

2. Discussion of Background

It is known that chemo- and biosensor elements are integrated in circulatory systems. The best known example is flow injection analysis (FIA) (e.g.: G. Schwedt: Taschenatlas der Analytik, Georg Thieme Verlag Stuttgart, 1992).

Similar devices are used as microdialysis systems for determining the glucose concentration in human tissue (e.g.: F. J. Schmidt et al.: Calibration of a wearable glucose sensor, The International Journal of Artificial Organs, Vol. 15, No. 1, 1992, Pages 055–061).

It is likewise known that chemo- and biosensor elements which operate with polymeric membranes and gel layers for substance recognition, can be produced in silicon technology according to the containment principle (DE 41 15 414 A1). In this respect the polymeric membranes and gel layers are not produced on the surface of silicon chips but in the interior of the chip. Compared to planar structures, this has considerable advantages as regards simplicity of manufacture and long-term stability.

These sensors can also be incorporated in silicon technology in prefabricated circulatory measuring cells.

A disadvantage of the described prior art is that until now no sensors have been described which operate on the containment principle and are incorporated in common with a circulatory measurement chamber on a chip.

SUMMARY OF THE INVENTION

Therefore the object underlying the invention is to integrate chemo- and biosensor elements according to the containment principle in common with a circulatory measurement chamber on a chip. The measuring chamber with the integrated sensors is to be produceable preferably in silicon technology, but also in other technology. In addition the sensors are to be capable of integration with the circulatory measuring chamber, e.g. in common with pumps, reaction paths, valves, etc. in microsystems.

Thus it is proposed according to the invention to dispose a duct-shaped cavity in a chip in such a way that it is contact with the smaller opening of the containment. Then the substance-recognition material inserted in the containment forms in the area of the small containment opening the active sensor surface, to which the liquid measuring medium is brought to the duct, and thus can come into contact with the sensor surface.

Preferably, in the circulatory measuring chamber, a Si substrate is used as a carrier. The invention however includes all other appropriate materials. The substance-recognition membrane materials usable for the sensor arrangement and the design of the containment and of the preferred Si carrier itself are known from DE 41 15 414. Therefore reference is made expressly to the disclosed content of this document.

There are preferably used as substance-recognition membrane materials those which, due to their flow behaviour through one of the openings, preferably the large opening, can be brought in on the front-side surface into the containment. Filling may for example be effected by means of an automatic dispenser device according to the ink jet principle, or also according to the method described in DE 41 15 414.

All the immobilizing materials previously known from prior art can be used for potentiometric and in particular amperometric biosensors. Examples of these are gelatin, collagen, alginate, agar, cellulose. triacetate, silicon rubber, polyvinyl alcohol, polyurethane, HEMA and all other known materials. Photolinkable materials can be cross-linked by UV radiation after filling through the upper or lower containment opening.

The active substance-recognition components such as enzymes or antibodies are immobilised in these materials. This may be effected according to known methods, such for example as F. Scheller, F. Schubert: Biosensors, Birkhauser Verlag, Berlin, 1989. The electrical contact layers which in fact lead into the containment filled with the substance-recognition membrane material, preferably are composed of films of noble metals such as platinum, gold or silver.

Likewise all other films can be used which are generated by the known thin-layer technology such as evaporating or sputtering and then photolithographic structuring. It is also possible to evaporate on or sputter on these metal film structures through shadow masks or to spray them on through a solution according to the electrospray method. Instead of the noble metals, however electrically conductive materials such as graphite or others can also be used. It is advantageous for the circulatory measuring chamber, as also described in DE 41 15 414, to cover the substrate with an insulating layer. Particularly suitable for this purpose are $SiO_2$ and/or other dielectrics such for example as $Si_3N_4$ It is further preferred to provide at least the upper side containment opening with an encapsulating layer.

According to the invention a carrier described as above, preferably an Si carrier, is connected with the inserted containments by the second surface by means of at least one plate, the inserted cavity being so formed that it is in contact with the smaller opening of the containment. Preferably, the duct-shaped cavity is inserted on the side of the Si carrier upon which the smaller opening of the containment is located. In this way only one duct structure can be formed which is in contact with the smaller opening of the containment. Alternatively, it is however also possible to incorporate the duct-shaped cavity, not behind the Si carrier, but in the plate connected to the Si carrier. The essential factor is that in each case a contact is produced between the duct-shaped cavity and the smaller opening of the containment. Therefore the duct-shaped cavity can be so formed that it is made by recesses both in the Si carrier and in the plate. The plate itself can consist either of glass, photostructurable glass, ceramic, green tape, plastic or other appropriate material. In a further development of the invention, metal films are incorporated in the duct-shaped recesses as electrodes by means of the known thin-layer technology.

The invention further relates to a method of manufacturing the miniaturized circulatory measuring chamber described above. The procedure in this method can be such that either the duct-shaped cavity is incorporated in the second surface of the Si wafer, and then this duct-shaped cavity is closed by means of a plate, or an appropriate structure is inserted in the plate and this latter is connected to the second surface of the carrier.

The insertion of the containment into the wafer is basically known from DE 41 15 414, with the example of the Si wafer. In this respect the invention also includes this previously known method for manufacturing the containment structure.

The formation of the duct structure in the second surface of the wafer is preferably effected by anisotropic or isotropic etching processes. The subsequent closure of the duct is effected according to the method of anodic bonding with a plate, e.g. a glass lid, so that an entirely covered duct results, through which the measuring medium can then be brought on to the active surface of the sensor. The duct structured in the wafer can also be covered by a polymer film of photostructurable dry resist by lamination, or with a plastic film which is connected to the plate-shaped carrier by means of an adhesive.

When the duct-shaped recess is to be located in the plate itself, this latter may be effected for example by etching, and the plate thus structured connected to the wafer by means of anodic bonding. As already stated above, it is also possible to combine the two variant methods described above, i.e. on the one hand to produce a recess both in the second surface of the wafer and on the other hand to produce a recess in the plate and thus make a cavity.

The measurements to be carried out with this apparatus may be carried out in a known way, depending on the analyte and substance-recognition membrane material, according to the potentiometric or amperometric principle. For this purpose the measuring chamber with the chemo- or biosensor is preferably inserted in a FIA arrangement. It is however just as possible to use the measuring chamber and sensor in other circulatory apparatus. In addition, the sensors with the circulatory measuring chamber can be integrated with the aid of the known microstructure technologies in common with pumps, reaction paths, valves and other system components in Microsystems.

The advantages achieved by the invention reside in particular in the fact that sensor and circulatory chamber are produced on a carrier (chip) and thus integration of chemo- and biosensors is possible in Microsystems. Thus the known advantages of microstructure technology as regards feasibility of mass production, reliability and capacity for miniaturizing can be utilised.

BRIEF DESCRIPTION OF THE DRAWINGS

Further features, details and advantages of the invention will become apparent from the following description of preferred embodiments of the invention, and with reference to the drawings, which show.

DETAILED DESCRIPTION

Figure 1:
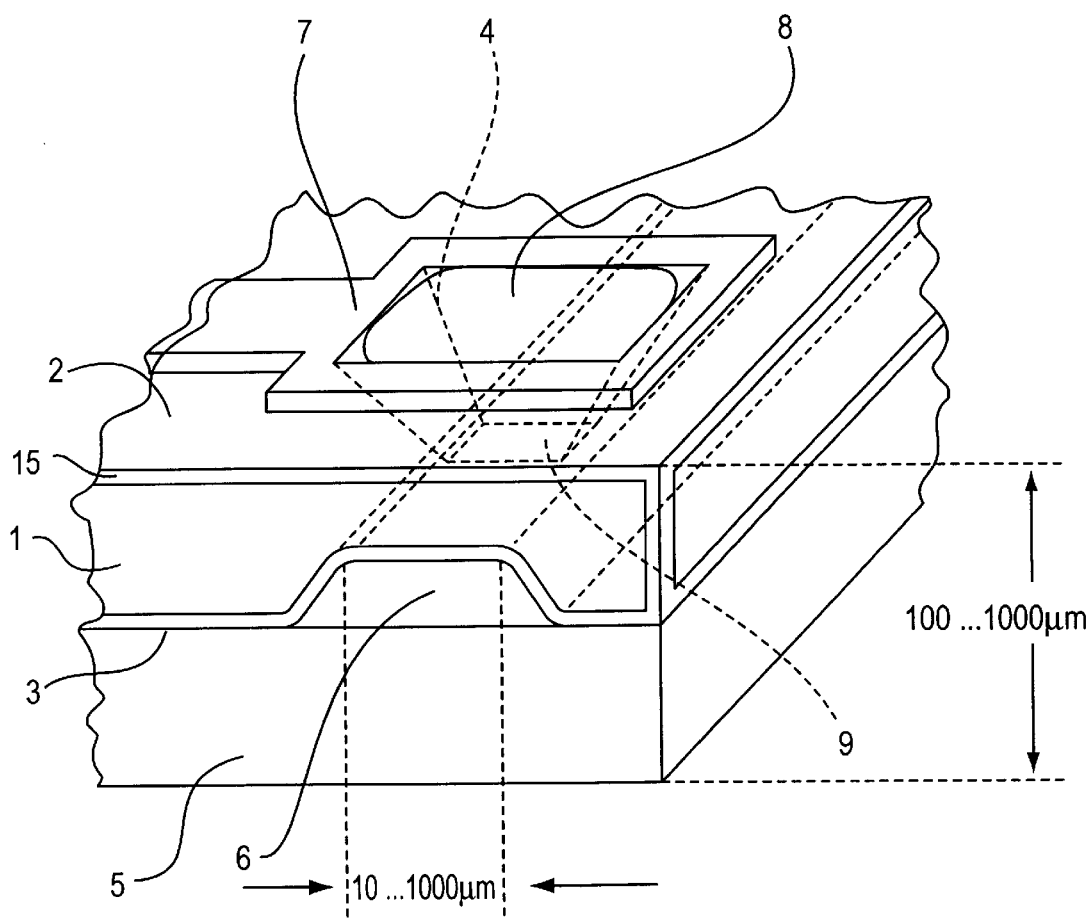
FIG. 1: a sensor according to the containment principle with a duct structure in the Si carrier, in a perspective view.

FIG. 1 shows a sensor according to the containment principle comprising a silicon wafer 1 with containment structure 4, metal film 7 and a substance-recognition membrane material 8. The manufacturing process is known from DE 41 15 414. In this the silicon is covered with an insulating coating 15 of $SiO_2$ and if necessary additionally with another dielectric ($Si_3N_4$). The containment 4 is in a tapering structure from the frontal surface 2 to the second surface 3.

Before or after production of this sensor structure, the duct-shaped recess 6 is produced in the silicon by known anisotropic or isotropic etching processes. After the method of anodic bonding, this duct 6 is closed by a glass lid 5, so that a covered duct results, through which the measuring medium can be passed over the active surface of the sensor (small opening 9). The dimensions of the duct lie in the range of 10 to 1,000 µm, depending on requirements, the overall height of the chip comes to 100 to 1,000 µm.

Figure 2:
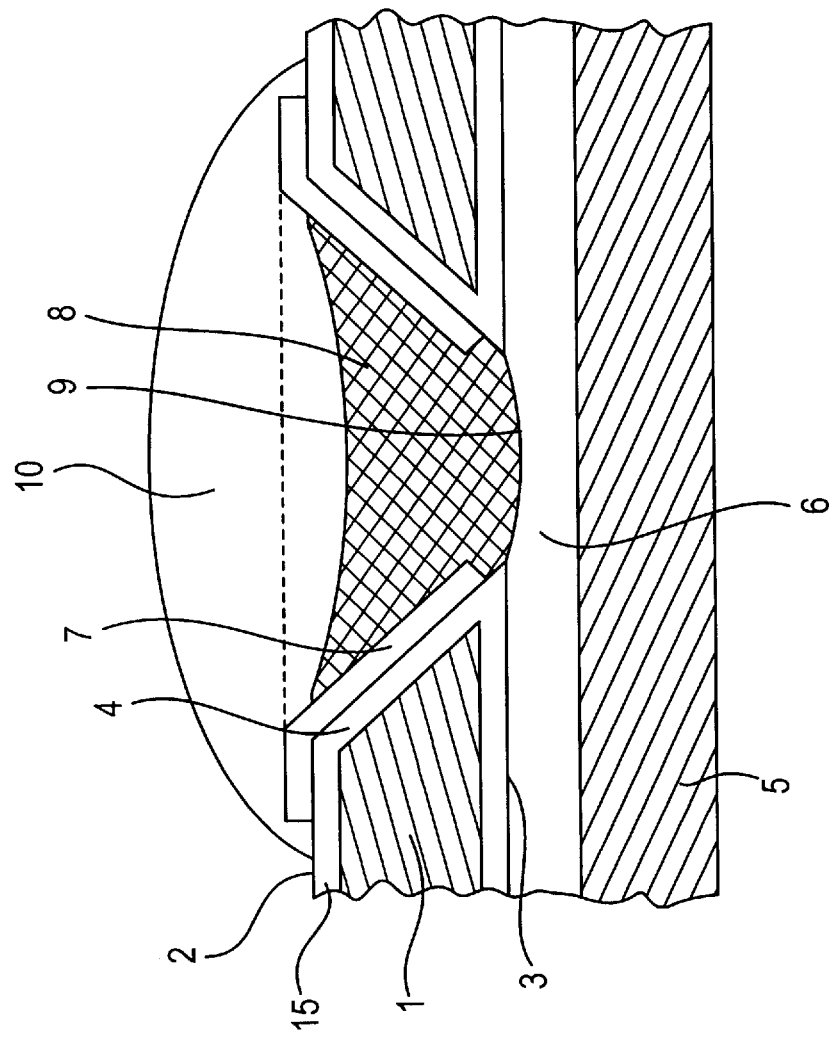
FIG. 2: a cross-section of the apparatus in FIG. 1.

In FIG. 2, the arrangement according to FIG. 1 is shown in cross-section. The cross-section extends along the duct-shaped recess. In addition to FIG. 1, it is shown in FIG. 2 how the membrane-filled containment structure is covered with an encapsulating layer 10.

Figure 3:
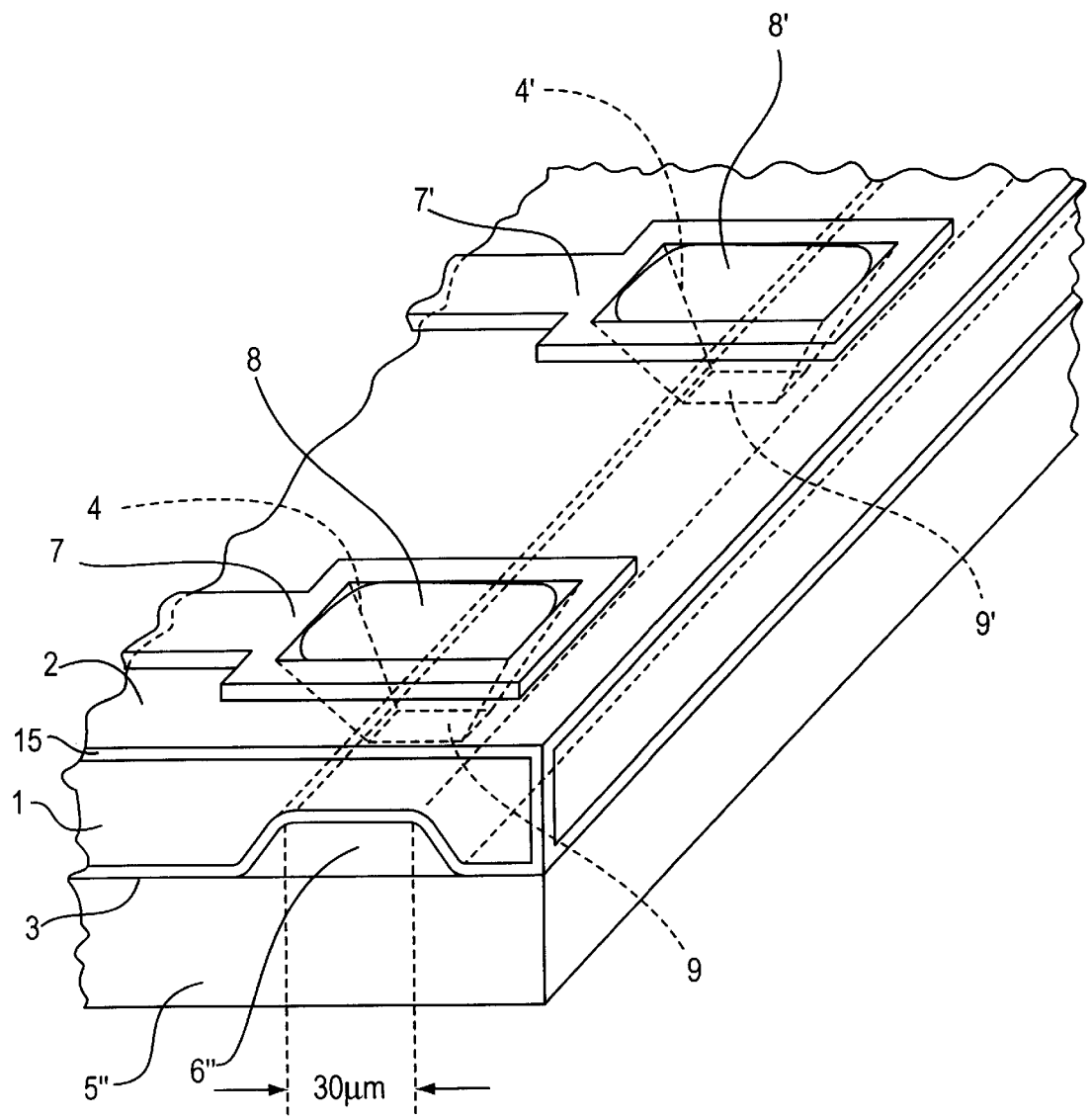
FIG. 3: a sensor according to the containment principle analogous to FIG. 1 in a perspective view, yet with two containments.

FIG. 3 shows an arrangement with two containment sensors according to FIG. 1. The two active sensor surfaces (openings 9 and 9') in this case have contact with the measuring medium, which is passed through the duct (6").

Alternatively to the example in FIG. 1, in this case the cover for the duct (6"), is produced by a polymer film (5"). This film can for example be a photostructurable dry resist, which is laminated on according to the known method. The film may also however comprise a plastics film, which is connected to the plate-shaped carrier by adhesive.

For use as a glucose sensor, the substance-recognition membrane materials in the first containment (4) consist for example of gelatin with the enzyme GOD, and in the second containment (4') of gelatin without the enzyme GOD. Measurement is in this case effected according to the amperometric principle by application of an electrical voltage of approximately 0.6 volts respectively between the platinum films (7) and (7') and a reference electrode arranged externally or in the duct 6", and by measurement of the current.

If more than one containment structure is used in the circulatory arrangement, there results a multi-sensor system in a circulatory measuring chamber.

Figure 4:
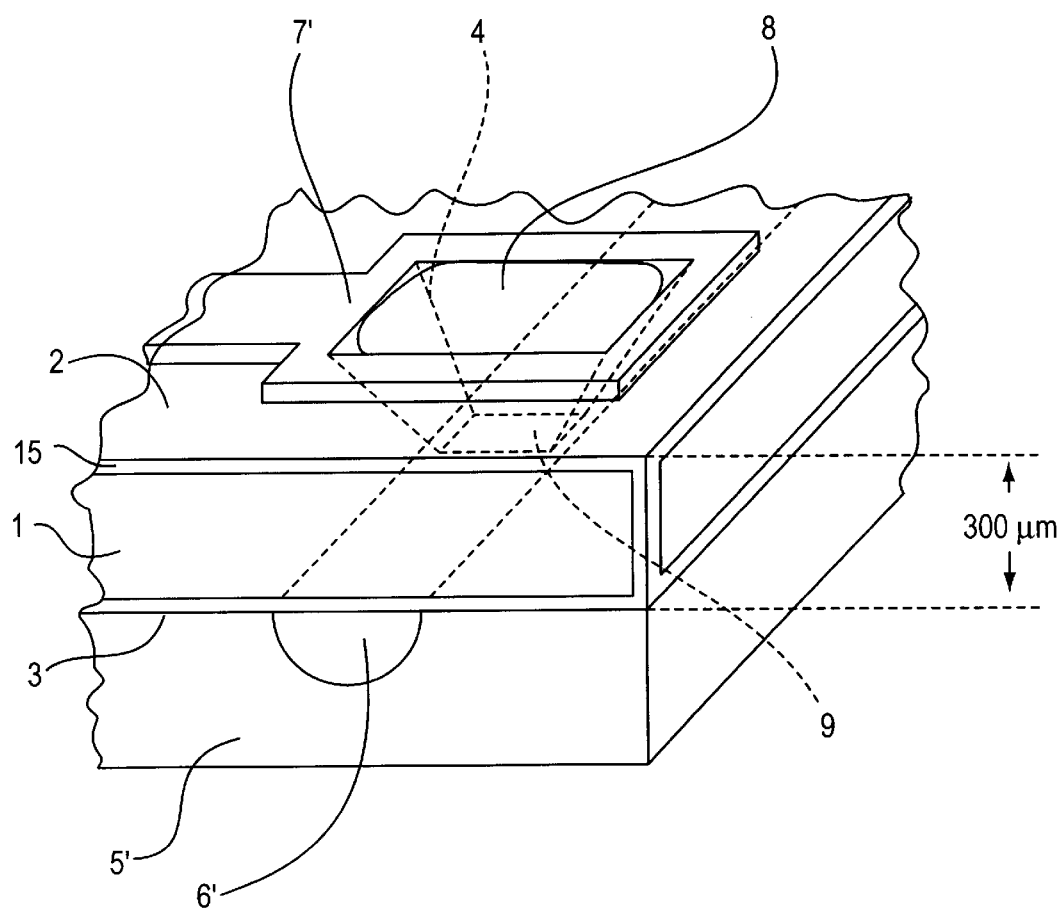
FIG. 4: a perspective view of a sensor according to the containment principle, the duct structure in this case being produced in the plate itself.

FIG. 4 shows an embodiment in which the duct-shaped recess (6') is produced for example by etching in the cover plate (5'). This cover plate, provided with the duct-shaped recess, is connected to the silicon wafer by anodic bonding. The Si wafer in this case has a thickness of 300 µm.

Metallic films may also be inserted in the duct-shaped recesses according to FIGS. 1 to 4 as electrodes (not shown). If for example a silver film is applied to the inner wall of the duct and electrolytically chloridated, there is obtained an Ag/AgCl—reference electrode, by means of which measurements may be carried out potentiometrically or amperometrically against one or more containment sensors.

Alternatively to the embodiments in FIGS. 1 to 4, the plate-shaped carrier may also comprise glass, ceramics, green tape, plastics or other materials.

Figure 5:
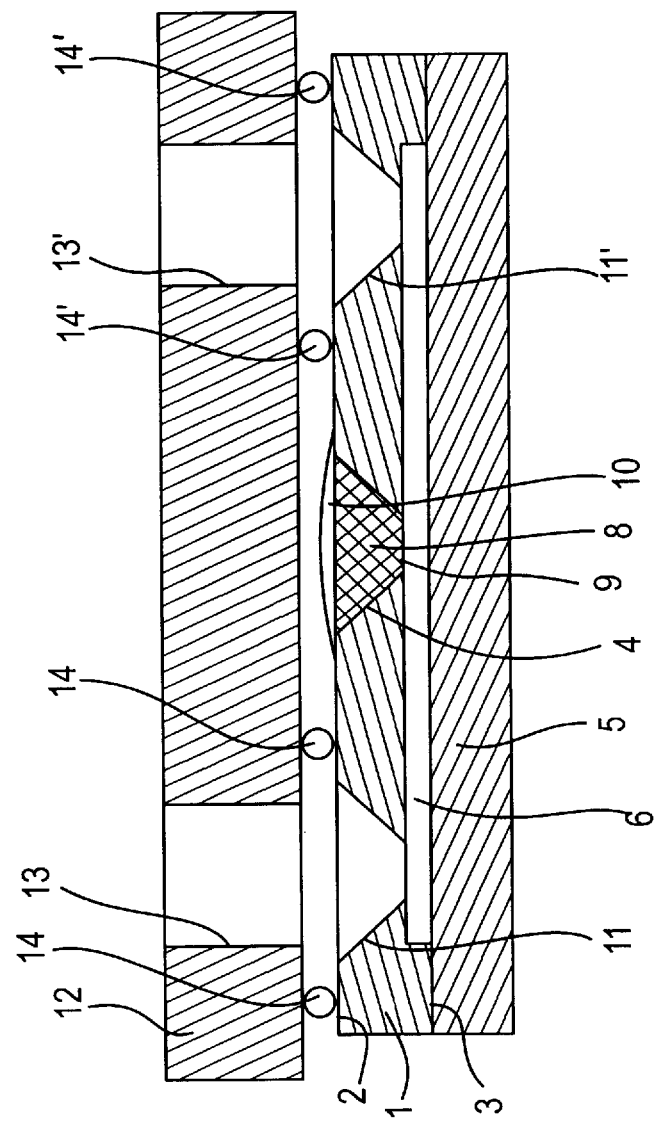
FIG. 5: a simplified view of the possible methods of introduction and removal of the liquid medium.

A possible means of introduction and removal of the liquid measuring medium is shown in FIG. 5.

For reasons of simplicity, the sensor is shown with the containment (4), the substance-recognition membrane material (8) and the encapsulating layer (10), but without insulating layers (15) and metal films (7).

In this case the duct-shaped recess (6) of the circulatory arrangement is connected with at least two openings (11)

and (11'), which connect the duct-shaped recess with the first surface (2) of the silicon wafer.

This circulatory arrangement is connected to a plastic block 12, which has at least two openings (13) and (13'), through which the liquid measuring medium is introduced and removed. Seal rings (14) and (14') are provided for sealing between the silicon chip and the plastic block.

I claim:

1. A miniaturized circulatory measuring chamber integrated with one of a chemosensor and a biosensor, comprising:
    a carrier plate having a frontal surface and a second surface;
    at least one containment formed in the carrier plate which tapers from the frontal surface to the second surface, the at least one containment having an opening;
    a substance-recognition material within the at least one containment;
    at least one supplementary plate connected to the second surface of the carrier plate; and
    at least one duct located in a region of at least an interface between the carrier plate and the at least one supplementary plate, the at least one duct communicating with the opening of the at least one containment.

2. The miniaturized circulatory measuring chamber of claim 1, wherein the substance-recognition material forms an active sensor surface in a region of the at least one containment opening.

3. The miniaturized circulatory measuring chamber of claim 1, wherein the substance-recognition material comprises a substance-recognition membrane material, and wherein the at least one containment is closed by an encapsulating layer.

4. The miniaturized circulatory measuring chamber of claim 1, wherein the at least one duct is further located in the carrier plate.

5. The miniaturized circulatory measuring chamber of claim 1, wherein the at least one duct is further located in the at least one supplementary plate.

6. The miniaturized circulatory measuring chamber of claim 1, wherein the opening of the at least one containment forms a lower opening, and wherein the at least one containment also has an upper opening, and wherein a photo-linkable substance-recognition material is cross-linked by UV radiation after entering the at least one containment through one of the upper containment opening and the lower containment opening.

7. The miniaturized circulatory measuring chamber of claim 1, further comprising pumps, reaction paths, and valves for circulating a liquid measuring medium past the at least one containment.

8. The miniaturized circulatory measuring chamber of claim 1, wherein the substance-recognition material comprises a substance-recognition membrane material which is contained in the at least one containment and which is immobilized in an immobilizing material.

9. The miniaturized circulatory measuring chamber of claim 8, wherein the substance-recognition material is at least one member selected from the group consisting of enzymes and antibodies.

10. The miniaturized circulatory measuring chamber of claim 1, wherein the carrier plate comprises Si covered with an insulating layer, and wherein at least one electrical contact layer leads to the at least one containment, and wherein the substance-recognition material comprises a substance-recognition membrane material which is contained within the at least one containment.

11. The miniaturized circulatory measuring chamber of claim 10, wherein the at least one electrical contact layer comprises a film of noble metal.

12. The miniaturized circulatory measuring chamber of claim 11, wherein the noble metal is selected from the group consisting of platinum, gold, and silver.

13. The miniaturized circulatory measuring chamber of claim 10, wherein the at least one electrical contact layer comprises graphite.

14. A miniaturized circulatory measuring chamber integrated with one of a chemosensor and a biosensor, comprising:
    a carrier plate having a frontal surface and a second surface, the carrier plate including:
        at least one containment formed in the carrier plate which tapers from the frontal surface to the second surface, the at least one containment having an opening,
        a substance-recognition material within the at least one containment, and
        at least one duct recess communicating with the opening of the at least one containment; and
    at least one supplementary plate connected to the second surface of the carrier plate such that the at least one supplementary plate and the at least one duct recess form at least one duct communicating with the opening of the at least one containment.

15. A method of using a miniaturized circulatory measuring chamber wherein the method comprises integrating the measuring chamber with at least one of a chemosensor and a biosensor including: a carrier plate having a frontal surface and a second surface, at least one containment formed in the carrier plate which tapers from the frontal surface to the second surface, the at least one containment having an opening, a substance-recognition material associated with the at least one containment, at least one supplementary plate connected to the second surface of the carrier plate, and at least one duct located in a region between the carrier plate and the at least one supplementary plate, the duct communicating with the opening of the at least one containment;
    wherein an analyte is measured in the duct depending upon the analyte and the substance-recognition material, by at least one of amperometric and/or potentiometric techniques.

16. The method of claim 15, wherein the measuring is performed in a flow-injection analysis arrangement.

17. A method for producing a miniaturized circulatory measuring chamber integrated with one of a chemosensor and a biosensor including: a carrier plate having a frontal surface and a second surface, at least one containment formed in the carrier plate which tapers from the frontal surface to the second surface, the at least one containment having an opening and substance-recognition material having an active surface associated with the at least one containment, at least one supplementary plate connected to the second surface of the carrier plate, and at least one duct located in a region between the carrier plate and the at least one supplementary plate, the at least one duct communicating with the opening of the at least one containment, the method comprising:
    forming the at least one containment in the carrier plate;
    forming at least one duct recess in the second surface of the carrier plate by etching; and
    covering the at least one duct recess by bonding the carrier plate to the at least one supplementary plate to form the at least one duct, such that a liquid measuring medium is capable of passing through the at least one duct and over the active surface of the substance-recognition material.

18. The method of claim 17, wherein the carrier plate comprises Si.

19. The method of claim 17, wherein the etching comprises anisotropic etching.

20. The method of claim 17, wherein the etching comprises isotropic etching.

21. The method of claim 17, wherein the at least one supplementary plate comprises a glass lid which is anodically bonded to the carrier plate.

22. The method of claim 17, wherein the at least one supplementary plate comprises a polymer film of a photostructurable dry resist laminated to the carrier plate.

23. The method of claim 17, wherein the at least one supplementary plate comprises a plastic film which is bonded to the carrier plate by adhesive.

24. The method of claim 17, further comprising forming metal film electrodes in the at least one duct by a thin-layer method.

* * * * *